(12) United States Patent
Güller et al.

(10) Patent No.: US 6,709,584 B2
(45) Date of Patent: Mar. 23, 2004

(54) DEVICE FOR ANALYZING SUBSTANCES BY MEANS OF THIN LAYER CHROMATOGRAPHY

(75) Inventors: Rolf Güller, Herznach (CH); Séraphin Munch, Rixheim (FR); Philippe Jablonski, St. Louis (FR); Josef Schröer, Bottmingen (CH)

(73) Assignee: Chemspeed Ltd., Augst (CH)

( * ) Notice: Subject to any disclaimer, the term of this patent is extended or adjusted under 35 U.S.C. 154(b) by 27 days.

(21) Appl. No.: 10/182,551

(22) PCT Filed: Jan. 29, 2001

(86) PCT No.: PCT/CH01/00066
§ 371 (c)(1),
(2), (4) Date: Jul. 30, 2002

(87) PCT Pub. No.: WO01/59445
PCT Pub. Date: Aug. 16, 2001

(65) Prior Publication Data
US 2003/0013187 A1 Jan. 16, 2003

(30) Foreign Application Priority Data
Feb. 14, 2000 (CH) ................................. 294/00

(51) Int. Cl.$^7$ ................................. B01D 15/08
(52) U.S. Cl. ..................... 210/198.3; 210/658
(58) Field of Search ............... 210/658, 198.3; 422/70; 436/162, 178; 73/61.54

(56) References Cited

U.S. PATENT DOCUMENTS

| | | | | |
|---|---|---|---|---|
| 3,327,857 A | | 6/1967 | Kopp et al. ............... | 210/198.2 |
| 3,342,333 A | * | 9/1967 | Geiss et al. ................ | 210/94 |
| 3,477,950 A | * | 11/1969 | Clement et al. ............ | 210/658 |
| 3,501,009 A | * | 3/1970 | Jaworek .................... | 210/198.3 |
| 3,516,546 A | | 6/1970 | Clark, III .................. | 210/198.2 |
| 3,738,493 A | * | 6/1973 | Cummins et al. .......... | 210/198.3 |
| 3,752,316 A | * | 8/1973 | Takeshita .................. | 210/198.3 |
| 3,919,082 A | * | 11/1975 | Falk ........................... | 210/658 |
| 4,272,381 A | * | 6/1981 | Kremer et al. ............. | 210/658 |
| 4,348,286 A | * | 9/1982 | Felton ........................ | 210/658 |
| 4,781,892 A | * | 11/1988 | Dickakian .................. | 422/69 |
| 4,827,780 A | * | 5/1989 | Sarrine et al. ............. | 73/864.21 |
| 6,096,205 A | * | 8/2000 | Haas et al. ................. | 210/198.3 |
| 6,264,893 B1 | * | 7/2001 | Markoski ................... | 422/70 |
| 6,303,029 B1 | * | 10/2001 | Nurok et al. .............. | 210/198.3 |

FOREIGN PATENT DOCUMENTS

| | | |
|---|---|---|
| CH | 505 636 | 4/1971 |
| DE | 2 327 449 | 12/1974 |
| DE | 44 08 172 A1 | 9/1995 |

OTHER PUBLICATIONS

"CAMAG Automatic Developing Chamber (ADC)" 1pg., undated.
Abstract of JP 58 113858 published Jul. 6, 1983.

* cited by examiner

Primary Examiner—Ernest G. Therkorn
(74) Attorney, Agent, or Firm—Leydig, Voit & Mayer, Ltd.

(57) ABSTRACT

A device for analyzing substances by thin layer chromatography comprises a solvent trough with two solvent channels, wherein two wall plates are mounted in the solvent trough, enabling thin layer plates to be arranged obliquely with respect to the horizontal in the solvent channels. The substance to be analyzed can thus be dropped or applied onto the thin layer plates from above, and solvent can be supplied to the solvent channels from above at a solvent supply point. The upward migration of components of the substance to be analyzed can thus be started without changing the position of the thin layer plate for this purpose.

18 Claims, 4 Drawing Sheets

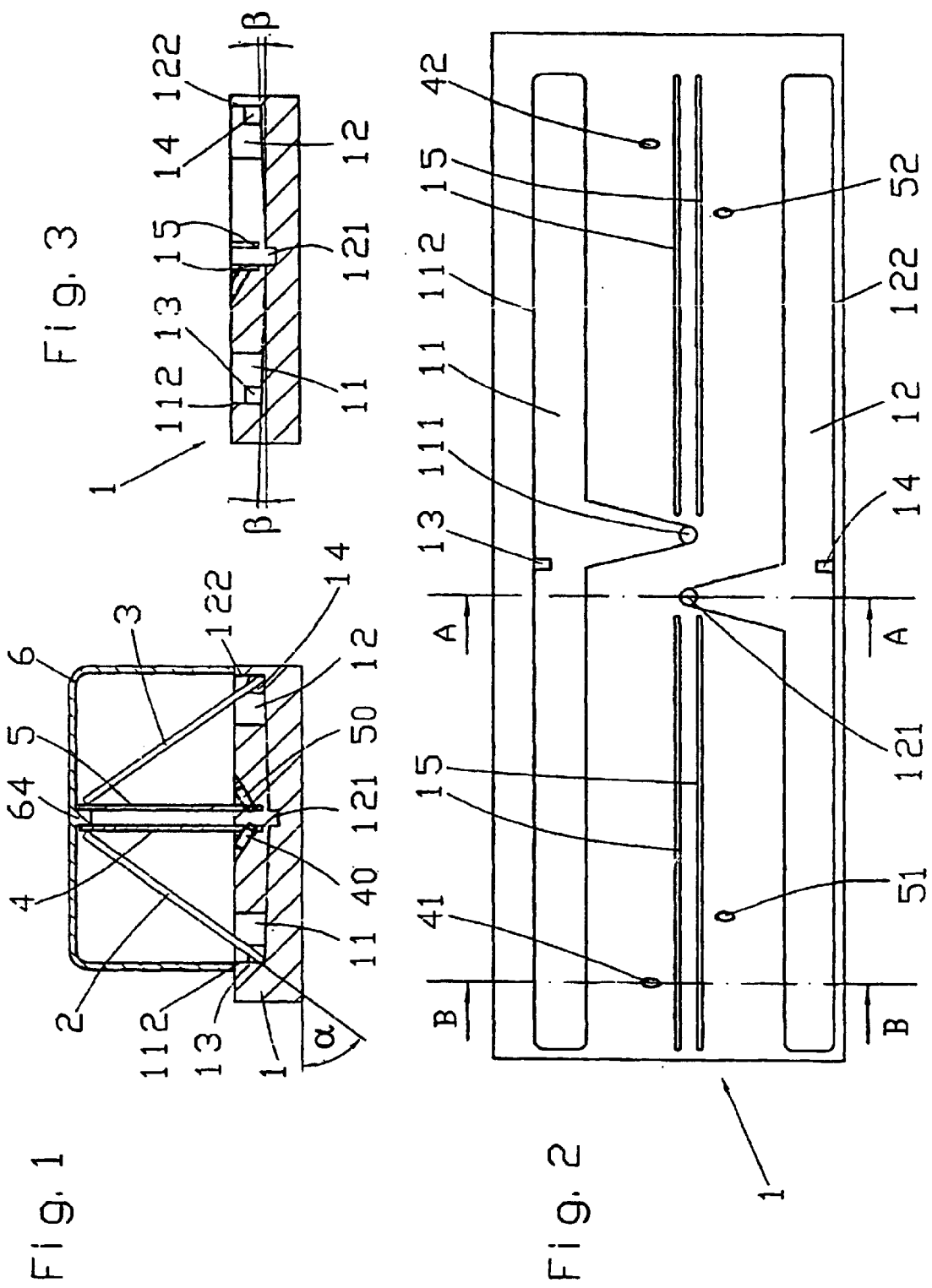

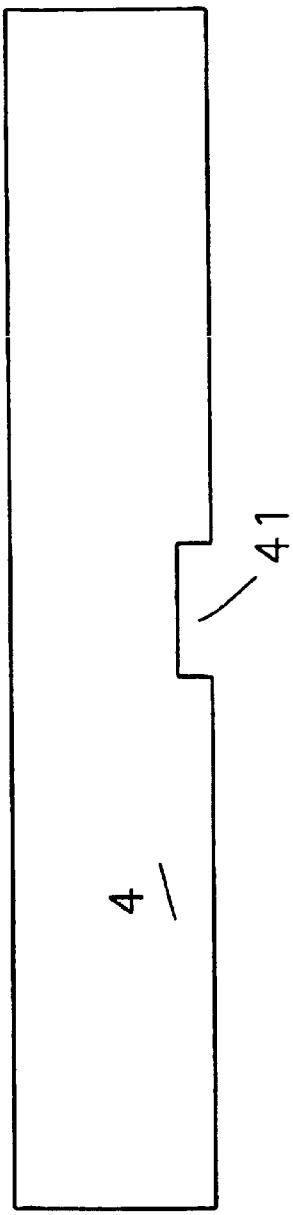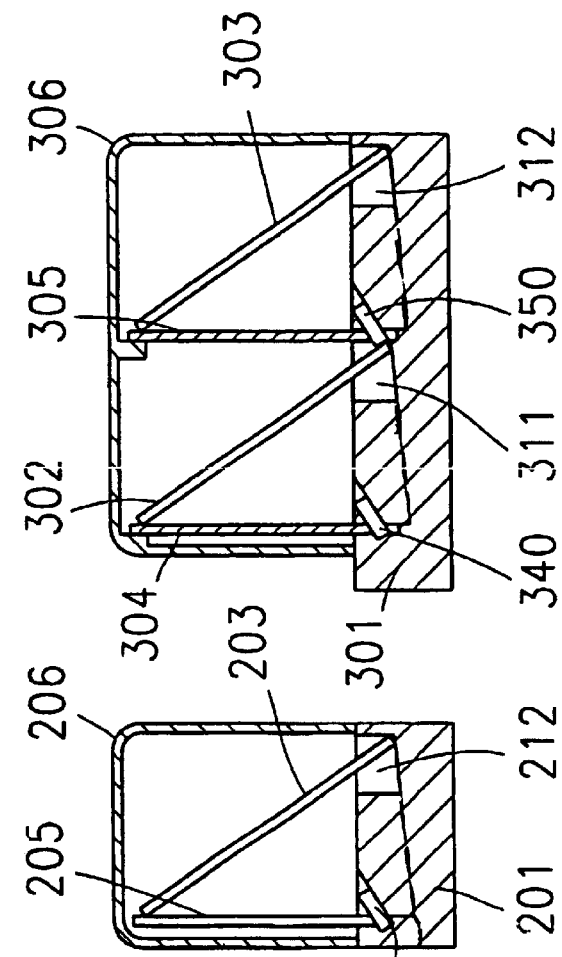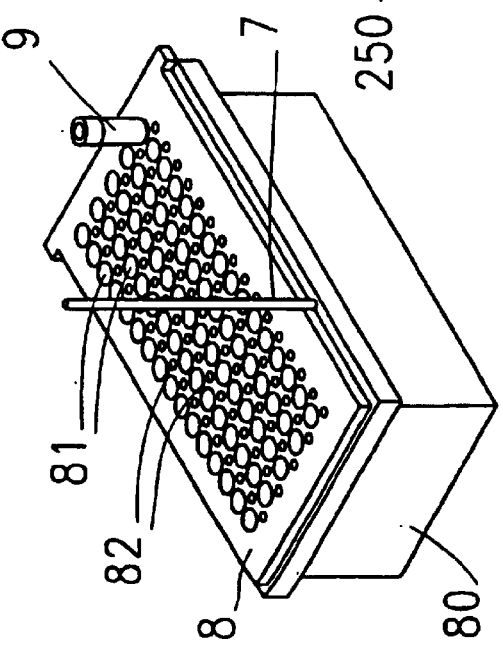

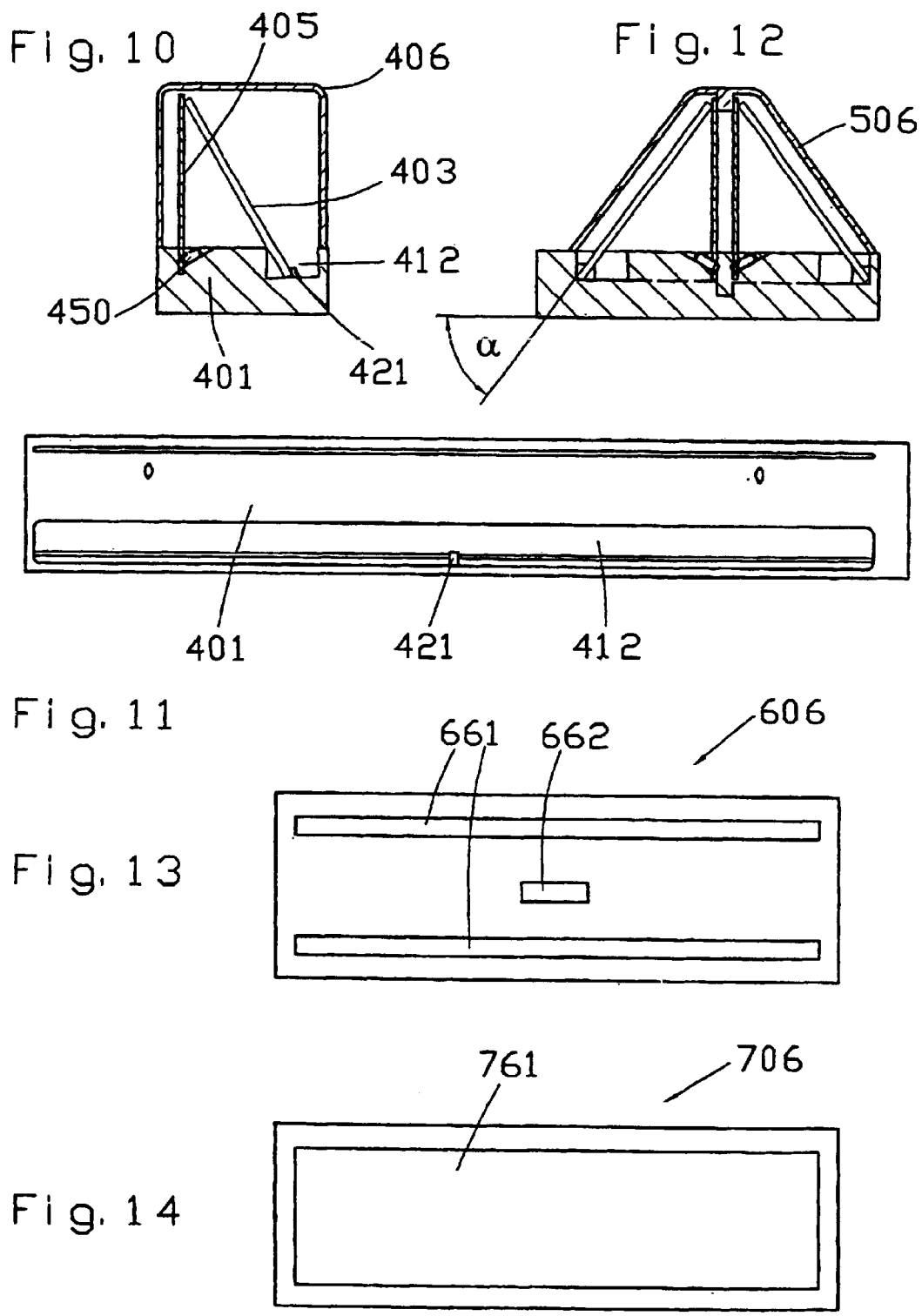

DEVICE FOR ANALYZING SUBSTANCES BY MEANS OF THIN LAYER CHROMATOGRAPHY

REFERENCE TO RELATED APPLICATIONS

This application is a 371 of PCT/CH01/00066 filed Jan. 29, 2001.

The present invention relates to a device for analyzing substances by means of thin layer chromatography.

During the analysis of substances by means of thin layer chromatography, the substance to be analyzed is dropped or applied onto a thin layer plate, which has a support plate and, arranged thereon, a thin layer of a functional substance, for example silica gel, $C_{18}$, $C_8$, $C_4$, $C_2$, $C_6H_5$, $NH_2$, $Al_2O_3$, paper (cellulose), starch, etc. The thin layer plate is then placed in a suitable solvent, or generally a mixture of solvents, for example hexane, hexane and ethyl acetate in the ratio 1:2, cyclohexane and dichloromethane in the ratio 2:1 etc., which, because of the capillary action of the thin layer, migrates upward and entrains upward the substance to be analyzed that has been dropped on or applied, or at least various components of it. Since the various substances or components migrate upward over different distances, information can be obtained therefrom about the substance or the components, especially if a reference substance has likewise been applied.

To date, the analysis of substances by means of thin layer chromatography has usually been carried out manually. In this case, the thin layer plate is placed flat on the laboratory table and a drop of a reference substance and drop of the substance to be analyzed or, respectively next to one another, a drop of various substances to be analyzed, are applied onto the thin layer plate on a start line, for example using a pipette. The thin layer plate is then placed manually in a trough containing solvent, so that the lower part of the thin layer plate is wetted and the solvent can migrate upward, and in doing so it entrains upward the substance to be analyzed, or at least various components of it. So that the solvent on the thin layer plate does not evaporate too quickly, the solvent trough and the thin layer plate are covered with a trough cover. Before the solvent reaches the top of the thin layer plate, the latter is withdrawn from the solvent trough.

The analysis of substances by means of manual thin layer chromatography has the disadvantage that it is relatively elaborate and requires the presence of a chemist or laboratory assistant, which can be problematic especially since the upward migration of the solvent may last several hours, and the thin layer plate may possibly need to be withdrawn from the solvent trough in the middle of the night so that the result image does not become smeared.

These disadvantages can be partially avoided by means of the Automatic Developing Chamber "ADC" from the company Camag, CH-4132 Muttenz, which comprises a solvent trough with a solvent channel, a trough cover and means for automatically supplying and withdrawing solvent. The thin layer plate provided with a substance to be analyzed is placed in the developing chamber, the developing chamber is closed and, finally, solvent is automatically supplied and subsequently withdrawn. The substance to be analyzed, however, still needs to be dropped or applied onto the thin layer plate outside the automatic developing chamber, and the thin layer plate then needs to be picked up and placed in the developing chamber.

In view of the disadvantages of the previously known methods and devices described above for the analysis of substances by means of thin layer chromatography, the object of the invention is as follows. A device is to be provided for the analysis of substances by means of thin layer chromatography of the type mentioned in the introduction, which permits simplified, automatable conduct of the substance analysis.

The essence of the invention is that a device for analyzing substances by means of thin layer chromatography, with a solvent trough which has at least one solvent channel, has means which make it possible to arrange a thin layer plate standing obliquely with respect to the horizontal in the solvent channel so that a substance to be analyzed can be dropped or applied onto the thin layer plate from above, and solvent can be supplied to the solvent channel at a solvent supply point so that the upward migration of components of the substance to be analyzed can be started without the position of the thin layer plate needing to be changed for this purpose.

Owing to the fact that the thin layer plate is arranged obliquely with respect to the horizontal, its position does not need to be changed throughout the whole time, which simplifies the entire procedure and allows it to be automated without great outlay. Automation is furthermore facilitated by the fact that the supply of a substance to be analyzed can take place from above, and commercially available robots that can be moved in one or two horizontal directions and the vertical direction can hence be used for this. Since these robots generally also carry out steps for the preceding and subsequent processes, it is highly advantageous to use them as well for the analysis of substances by means of thin layer chromatography, which may also be done on-line.

In a preferred embodiment, the solvent can furthermore be supplied from above.

The optimum angle $\alpha$ between the thin layer plate and the horizontal is between 40° and 50°, preferably 45°. At such an angle, on the one hand, the substance to be analyzed can easily be dropped on or applied from above and, on the other hand, the lower part of the thin layer plate can be wetted in a suitable way with the solvent, which can migrate upward properly together with the substance to be analyzed or components of it. In general, an angle $\alpha$ between 20° and 80°, or even between 5° and 85°, is suitable, while an angle $\alpha$ less than or equal to 5° and greater than 1°, or greater than or equal to 85° and less than 89°, is albeit less suitable but nevertheless possible.

Advantageously, the solvent trough has two or more mutually independent solvent channels, with at least two thin layer plates preferably being arrangeable in a solvent channel. It is also entirely feasible to implement ten or more solvent channels, with each feeding solvent to one thin layer plate. A plurality of substances can then be analyzed using two or more different solvents.

In a preferred embodiment, the or each solvent channel is inclined toward a solvent extraction point, which preferably coincides with the solvent supply point. This makes it possible not only to supply solvent at a single point, but also to subsequently extract solvent at a single point, preferably the same point. The migration process is started when the solvent is supplied, and it is terminated when the solvent is withdrawn.

In the normal case, the device according to the invention furthermore has a trough cover, which substantially seals the solvent channel or the solvent channels and the thin layer plate or plates from the outside. In this way, it is possible to produce a saturated atmosphere, which prevents excessively rapid evaporation of the solvent or solvents, especially if the vapor pressure is high at the analysis temperature.

Advantageously, the trough cover has at the top holes or slots or an open face, which make it possible to supply solvent and drop or apply substances to be analyzed onto the thin layer plate or plates through the trough cover, with the holes, slots or the open face preferably being closed by septa or a septum plate. The substance to be analyzed and solvents can hence be supplied from above when the solvent trough is covered, with sealed coverage being ensured by the septa or septum plates that are present if applicable.

Normally, the device according to the invention also comprises a delivery instrument, which preferably comprises a hollow needle that can be moved vertically and in at least one horizontal direction, by which substances to be analyzed can be dropped or applied automatically onto the thin layer plate or plates and solvents can be supplied automatically at the solvent supply point or points and can be extracted automatically at the solvent extraction point or points. The delivery instrument permits automatic handling of the substances and solvents so that, after the control unit of the delivery instrument has been programmed, the entire method can proceed without a chemist or laboratory assistant needing to intervene.

In a preferred embodiment, the device according to the invention has a reagent matrix, which comprises reception holes for reagent containers and delivery holes passing through between them, through which a delivery and withdrawal tool for delivering and withdrawing substances to be analyzed and solvents can be fed. Reagent containers containing substances to be analyzed can then simply be arranged in the reception holes and, for the analysis, a substance to be analyzed can be withdrawn from the reagent container and applied onto a thin layer plate arranged underneath through a delivery hole. In the normal case, solvents are withdrawn from separate large containers, although they may also be supplied in a different way instead of with said delivery and withdrawal tool, e.g. by pumping, opening a valve etc.

Advantageously, there are means for visualizing the components of the substance to be analyzed that have migrated upward, which preferably comprise a UV lamp and/or means for spraying with chemical reagents. The analysis result can hence be made directly visible.

In a preferred embodiment, the device according to the invention is furthermore provided with means for determining the time at which the solvent that is present needs to be withdrawn from the solvent channel or channels, which preferably comprise a CCD camera. The optimum time for withdrawing the solvent can hence be determined automatically, and the solvent can then be withdrawn automatically, without a chemist or laboratory assistant needing to be present for this purpose. Furthermore, in this embodiment, the time for withdrawing the solvent does not need to be pre-programmed, i.e. estimated.

The device according to the invention for the analysis of substances by means of thin layer chromatography will be described in more detail below with reference to the appended drawings with the aid of seven exemplary embodiments.

BRIEF DESCRIPTION OF THE DRAWINGS

FIG. 1 shows a sectional view of a first exemplary embodiment of the device according to the invention for the analysis of substances by means of thin layer chromatography with two solvent channels;

FIG. 2 shows a plan view of the solvent trough of the device of FIG. 1;

FIG. 3 shows a sectional view of the solvent trough along the line A—A in FIG. 2;

FIG. 6 shows a side view of a wall plate of the device of FIG. 1;

FIG. 7 shows a perspective view of the device according to the invention with a reagent matrix, reagent container and hollow needle;

FIG. 8 shows a sectional view of a second exemplary embodiment of the device according to the invention for the analysis of substances by means of thin layer chromatography with a single solvent channel;

FIG. 9 shows a sectional view of a third exemplary embodiment of the device according to the invention for the analysis of substances by means of thin layer chromatography with two solvent channels;

FIG. 10 shows a sectional view of a fourth exemplary embodiment of the device according to the invention for the analysis of substances by means of thin layer chromatography with one solvent channel;

FIG. 11 shows a plan view of the solvent trough of the fourth exemplary embodiment;

FIG. 12 shows a sectional view of a fifth exemplary embodiment of the device according to the invention for the analysis of substances by means of thin layer chromatography with two solvent channels;

FIG. 13 shows a plan view of the trough cover of a sixth exemplary embodiment of the device according to the invention for the analysis of substances by means of thin layer chromatography with two solvent channels;

FIG. 14 shows a plan view of the trough cover of a seventh exemplary embodiment of the device according to the invention for the analysis of substances by means of thin layer chromatography with two solvent channels.

DESCRIPTION OF THE PREFERRED EMBODIMENTS

Figure 4:
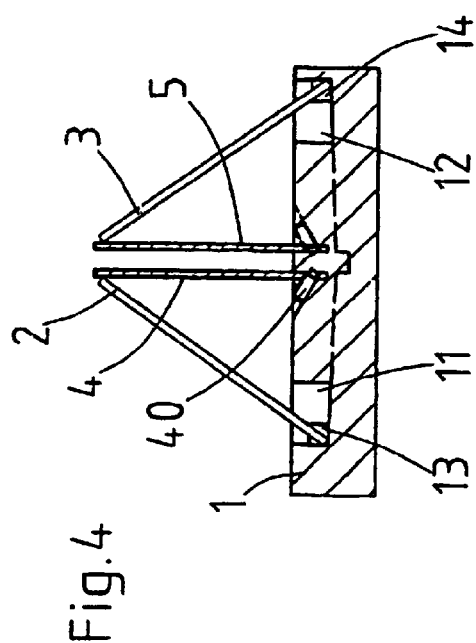
FIG. 4 shows a sectional view of the solvent trough along the line B—B in FIG. 2 with wall plates mounted therein and thin layer plates arranged therein.
Figure 5:
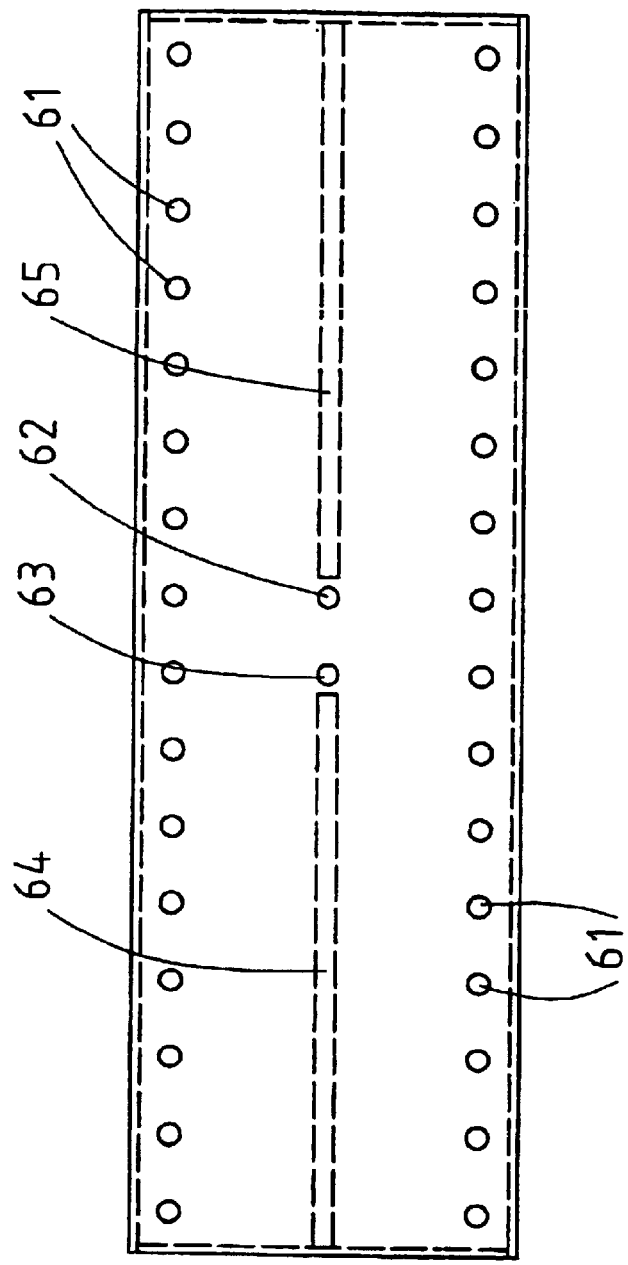
FIG. 5 shows a plan view of the trough cover of the device of FIG. 1.

First Exemplary Embodiment—FIGS. 1 to 7

The represented first exemplary embodiment of the device according to the invention for the analysis of substances by means of thin layer chromatography comprises a solvent trough 1, in which two wall plates 4 and 5 are mounted vertically by means of four threaded pins 40 and 50 arranged in threaded holes 41, 42, 51 and 52. To accommodate the wall plates 4, 5, the solvent trough 1 has grooves 15, into which the wall plates 4, 5 are fitted. In the central region, the wall plates 4, 5 respectively have a recess 41, into which the grooveless central region of the solvent trough 1 protrudes. The two wall plates 4, 5 are spaced apart from one another, so that a delivery and withdrawal tool, here a hollow needle 7, can be fed in-between to solvent supply points 111 and 121.

The solvent trough 1 has two separate solvent channels 11 and 12, which are respectively subdivided by a separating lug 13 and 14 into two halves, and in which the solvent supply points 111 and 121 are arranged. The solvent channels 11, 12 are supplied with solvent via the solvent supply points 111, 121, it being possible to deliver different solvents to the two solvent channels 11, 12. In the present exemplary embodiment, they are simultaneously used as solvent extraction points. So that maximally complete extraction of the solvent can take place, the solvent channels 11, 12 are inclined, on the one hand, at an angle β with respect to the longitudinal mid-axis of the solvent trough 1 and, on the other hand, also with respect to the transverse mid-axis, so that the solvent flows to the solvent supply and extraction points 111, 121.

In the normal case, up to four thin layer plates 2, 3 are placed obliquely in the solvent channels 11, 12, and they are supported on the bottoms and on the sides 112, 122 of the solvent channels 11, 12 and on the wall plates 4, 5. The inclination angle of the thin layer plates 2, 3, i.e. the angle a between the thin layer plates 2, 3 and the horizontal, is approximately 55° in the present case, which permits, on the one hand, straightforward dropping-on or application from above of the substance to be analyzed and, on the other hand, suitable wetting with solvent as well as good upward migration of the solvent together with the substance to be analyzed or components of it.

Over the solvent trough 1 and the thin layer plates 2, 3, a trough cover 6 is arranged which provides sealing from the outside, so that saturated atmospheres that prevent excessively rapid evaporation of the solvent on the thin layer plates 2, 3 can be set up on both sides of the two wall plates 4, 5. Two longitudinal ribs 64, 65 of the trough cover 6 engage between the wall plates 4, 5 and hence fix the trough cover 6 in the lateral direction. The trough cover 6 has holes 62 and 63, which permit introduction of the hollow needle 7 of a delivery instrument for delivering solvent to the solvent supply points 111, 121, as well as holes 61 which permit insertion of the hollow needle 7 for dropping or applying substances to be analyzed onto the thin layer plates 2, 3. The holes 61, 62, 63 are preferably closed by septa or a septum plate.

The solvent trough 1 with the thin layer plates 2, 3 and the trough cover 6 may, for example, as represented in FIG. 7, be arranged in a frame 80 below a reagent matrix 8, which comprises reception holes 81 for reagent containers 9 and delivery holes 82 passing through between them, through which the hollow needle 7 for delivering and withdrawing substances to be analyzed and solvents can be fed.

As the delivery instrument, it is possible to use a commercially available robot, which can be moved in one or two horizontal directions and the vertical direction, for guiding the needle 7.

Second Exemplary Embodiment—FIG. 8

In this second exemplary embodiment, a device according to the invention has, besides a trough cover 206, a solvent trough 201 with only one solvent channel 212, only one wall plate 205 fastened by threaded pins 250 and, normally, only two thin layer plates 203. In other regards, the discussion relating to the first exemplary embodiment applies.

Third Exemplary Embodiment—FIG. 9

In this third exemplary embodiment, a trough cover 306 and a solvent trough 301 are designed in such a way, and two wall plates 304, 305 are fastened by threaded pins 340, 350 in the solvent trough 301 in such a way, that the normally four thin layer plates 302, 303 stand parallel with one another. In other regards, the discussion relating to the first exemplary embodiment applies.

Fourth Exemplary Embodiment—FIGS. 10 and 11

In this fourth exemplary embodiment, a device according to the invention has, besides a trough cover 406, a solvent trough 401 with a solvent channel 412, a wall plate 405 fastened by threaded pins 450 and, normally, two thin layer plates 403. A solvent supply and extraction point 421 is here arranged in front of the wall plate 405, instead of behind it. In other regards, the discussion relating to the first exemplary embodiment applies.

Fifth Exemplary Embodiment—FIG. 12

In this fifth exemplary embodiment, a device according to the invention has a trough cover 506 with side walls that extend roughly parallel to the thin layer plate. In other regards, the discussion relating to the first exemplary embodiment applies.

Sixth Exemplary Embodiment—FIG. 13

In this sixth exemplary embodiment, a trough cover 606 has, instead of holes for the delivery and withdrawal tool, three slots 661, 662 which are preferably closed by septa or septum plates. In other regards, the discussion relating to the first exemplary embodiment applies.

Seventh Exemplary Embodiment—FIG. 14

In this seventh exemplary embodiment, a trough cover 706 has, instead of holes for the delivery and withdrawal tool, an open face 761 which is preferably closed by a septum plate. In other regards, the discussion relating to the first exemplary embodiment applies.

What is claimed is:

1. A device for analyzing substances by thin layer chromatography, comprising a solvent trough having at least one solvent channel, and means for arranging a thin layer plate to stand obliquely with respect to the horizontal in the solvent channel so that a substance to be analyzed can be dropped or applied onto the thin layer plate from above, and solvent can be supplied to the solvent channel at a solvent supply point so that the upward migration of components of the substance to be analyzed can be started without changing the position of the thin layer plate.

2. The device of claim 1, wherein the solvent can be supplied to the solvent channel from above.

3. The device of claim 1, wherein the means for arranging the thin layer plate to stand obliquely with respect to the horizontal in the solvent channel provides an angle α between the arranged thin layer plate and the horizontal between 1° and 89°.

4. The device of claim 3, wherein the means for arranging the thin layer plate to stand obliquely with respect to the horizontal in the solvent channel provides the angle α between 20° and 80°.

5. The device of claim 4, wherein the means for arranging the thin layer plate to stand obliquely with respect to the horizontal in the solvent channel provides the angle α of between 40° and 50°.

6. The device of claim 1, wherein the solvent trough has two or more mutually independent solvent channels, with at least two thin layer plates being arrangeable in a solvent channel.

7. The device of claim 6, having a space between the solvent trough and the trough cover that is subdivided by an intermediate wall, arranged between the two solvent channels, comprising two wall plates used simultaneously as support plates for thin layer plates.

8. The device of claim 1, having a solvent extraction point, which coincides with the solvent supply point.

9. The device of claim 8, wherein the or each solvent channel is inclined toward a solvent extraction point.

10. The device of claim 8, further comprising a delivery instrument, by which solvents can be extracted automatically from above at the solvent extraction point or points.

11. The device of claim 1, having a trough cover which substantially seals the solvent channel or the solvent channels and the thin layer plate or plates from the outside.

12. The device of claim 11, wherein the trough cover has at the top holes or slots or an open face, allowing the supply of solvent and the dropping or applying of substances to be analyzed onto the thin layer plate or plates through the trough cover, with the holes, slots or the open face being closed by septa or a septum plate.

13. The device of claim 1, further comprising a delivery instrument, by which substances to be analyzed can be dropped or applied automatically onto the thin layer plate or plates.

14. The device of claim 13, wherein the delivery instrument comprises a hollow needle that can be moved vertically and in at least one horizontal direction.

15. The device of claim 1, further comprising a delivery instrument, by which solvents can be supplied automatically at the solvent supply point or points.

16. The device of claim 1, having a reagent matrix comprising reception holes for reagent containers and delivery holes passing through between them, through which a delivery and withdrawal tool for delivering and withdrawing substances to be analyzed and solvents can be fed.

17. The device of claim 1, further comprising means for visualizing the components of the substance to be analyzed that have migrated upward.

18. The device of claim 1, further comprising means for determining the time at which the solvent that is present needs to be withdrawn from the solvent channel or channels.

* * * * *